United States Patent
Danley et al.

(10) Patent No.: US 6,565,723 B1
(45) Date of Patent: May 20, 2003

(54) ISOLATED GROUND SENSOR ACHIEVED USING ALUMINA COATING OVER SPINEL COATING

(75) Inventors: Blaine R. Danley, Linden, MI (US); Thomas G. Line, Flint, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/729,401

(22) Filed: Dec. 4, 2000

(51) Int. Cl.⁷ .............................................. G01N 27/407
(52) U.S. Cl. ...................... 204/429; 204/427; 427/125; 427/126.2; 427/126.4
(58) Field of Search .................. 204/421–429

(56) References Cited

U.S. PATENT DOCUMENTS

| | | | | |
|---|---|---|---|---|
| 4,225,634 A | * | 9/1980 | Tanaka et al. |
| 4,272,349 A | * | 6/1981 | Furutani et al. |
| 4,379,741 A | * | 4/1983 | Sano et al. |
| 4,626,337 A | * | 12/1986 | Hotta et al. |
| 4,629,535 A | * | 12/1986 | Oyama et al. |
| 5,472,591 A | * | 12/1995 | Saito et al. |

* cited by examiner

Primary Examiner—T. Tung
(74) Attorney, Agent, or Firm—Vincent A. Cichosz

(57) ABSTRACT

An exhaust gas sensor element has an electrolyte body, an inner electrode disposed on an inner surface of the electrolyte body, an outer electrode disposed on an outer surface of the electrolyte body, and a ground isolating coating disposed over the outer electrode. The ground isolating coating is typically alumina and extends from an active end of the electrolyte body toward an opposing end of the electrolyte body. The invention also includes a method for constructing a gas sensor element, the steps of which comprise forming an electrolyte body having an inner surface and an outer surface, applying an electrode ink to the inner surface to form an inner electrode and to the outer surface to form an outer electrode, and depositing a combination poison resistant/ground isolating coating, which is typically alumina, over the outer surface such that the combination coating extends from an active end of the electrolyte body toward an opposing end of the electrolyte body.

14 Claims, 2 Drawing Sheets

ISOLATED GROUND SENSOR ACHIEVED USING ALUMINA COATING OVER SPINEL COATING

TECHNICAL FIELD

This invention relates to exhaust gas sensors, and, more particularly, to an oxygen sensor design that incorporates a ground isolation coating over a poison resistance coating.

BACKGROUND OF THE INVENTION

Gas sensors are used to sense the presence of constituents of exhaust gases, and are typically used in a variety of applications that require qualitative as well as quantitative analysis of gases. In automotive applications, the direct relationship between the oxygen concentration in an exhaust gas and the air-to-fuel ratio of the fuel mixture supplied to the engine allows the gas sensor to provide oxygen concentration measurements for the determination of optimum combustion conditions, maximization of fuel economy, and management of exhaust emissions.

A conventional stoichiometric gas sensor typically consists of an ionically conductive solid electrolyte material, a porous electrode on the exterior of the sensor having a porous protective overcoat exposed to the exhaust gases, and a porous electrode on the interior surface of the sensor exposed to a known oxygen partial pressure. Sensors typically used in automotive applications use a yttria-stabilized zirconia-based electrochemical galvanic cell with porous platinum catalytic electrodes, operating in potentiometric mode, to detect the relative amounts of oxygen present in the exhaust generated by the automobile engine. When opposite surfaces of this galvanic cell are exposed to different oxygen partial pressures, an electromotive force is developed between the electrodes on the opposite surfaces of the zirconia wall, according to the Nernst equation:

$$E = \left(\frac{-RT}{4F}\right)\ln\left(\frac{P_{O_2}^{ref}}{P_{O_2}}\right)$$

wherein:
- E=electromotive force
- R=universal gas constant
- F=Faraday constant
- T=aboslute temperature of the gas
- $P_{O_2}^{ref}$=oxygen partial pressurre of the reference gas
- $P_{O_2}$=oxygen partial pressureof the exhaust gas Due to the large difference in oxygen partial pressure between fuel-rich and fuel-lean exhaust conditions, the electromotive force changes sharply at the stoichiometric point, giving rise to the characteristic switching behavior of these sensors. Consequently, these potentiometric gas sensors indicate qualitatively whether the engine is operating fuel-rich or fuel-lean, without quantifying the actual air-to-fuel ratio of the exhaust mixture.

In general, electrodes are constructed around a ceramic electrolyte, which conducts ionic oxygen. The electrolyte develops a voltage when the oxygen concentration varies on opposing sides of the electrolyte surfaces. To measure the oxygen concentration of the exhaust gas, one side of the electrolyte is exposed to the exhaust gas while the other side is kept in contact with air. The voltage across the electrolyte is a function of the difference in oxygen concentration.

The electrodes are typically protected from contamination and erosion as a result of direct exposure to exhaust gas by a single porous poison resistance coating. This poison resistance coating is customarily magnesium aluminate spinel that is flame-spayed, plasma-sprayed, co-sintered, or thermally deposited on top of the exhaust sensing electrode over the active area of the electrode. Generally, the materials and porosity are selected to prevent metal impurities, such as silicon (Si), lead (Pb), calcium (Ca), phosphorus (P), magnesium (Mg), iron (Fe), and zinc (Zn), from permeating the layer and interfering with the operation of the sensor.

Additional coatings are used to isolate the sensor electrical circuit from the vehicle by limiting current flow between the sensor element and shell in the event that the vehicle exhaust system and the sensor are at different electrical potentials. In the prior art, this isolation coating is typically a magnesium aluminate spinel that is plasma-sprayed, co-sintered, or thermally deposited over the electrode where it would contact the metallic sensor package thus preventing a electrical path between the sensor and vehicle exhaust system. Additional prior art has used non-conductive glass coatings. During operation, this layer prevents the flow of current to the electrode as long as the voltage difference between the sensor and vehicle exhaust system is below the dielectric strength value that defines what the coating is capable of withstanding. On the other hand, if the voltage difference exceeds the dielectric strength of the coating, the sensor will experience the increased flow of current. Upon experiencing this increased flow of current, the sensor output voltage can be offset which will be interpreted by the engine management system as incorrect readings of the air/fuel ratio.

There remains a need in the art to have improved ground isolation properties without additional manufacturing operations or additional components.

SUMMARY OF THE INVENTION

A sensor element for an exhaust gas sensing apparatus that incorporates an alumina coating is disclosed herein. The gas sensor comprises: an electrolyte having a tip and a protrusion; an inner electrode disposed on an inner surface of said electrolyte body; an outer electrode disposed on an outer surface of said electrolyte body from said tip toward said protrusion; a protective coating disposed over said outer electrode; and an alumina coating disposed over at least a portion of said protective coating.

The method of constructing the gas sensor comprises: forming an electrolyte body having a tip and a protrusion; applying an electrode ink to an inner surface of said electrolyte body to form an inner electrode; applying said electrode ink to an outer surface of said electrolyte body to form an outer electrode from said tip toward said protrusion; depositing a protective coating over said outer electrode; and depositing an alumina coating over at least a portion of said protective coating.

The above-described features and other features and advantages of the invention will be appreciated and understood by those skilled in the art from the following detailed description, drawings, and appended claims.

BRIEF DESCRIPTION OF THE DRAWINGS

The apparatus will now be described by way of example, with reference to the accompanying drawings, which are meant to be exemplary and not limiting.

DETAILED DESCRIPTION OF THE PREFERRED EMBODIMENT

A sensor element of a gas sensing apparatus is described below wherein a combination poison resistant/ground isolating coating is deposited on an outer surface of a sensor element to minimize the likelihood that transient voltage spikes will detrimentally affect the operation of the apparatus. It should be understood that although the gas sensor apparatus is described as being an oxygen sensing device, the apparatus could be a nitrogen oxides sensing device, a hydrogen sensing device, a hydrocarbon sensing device, or the like.

The combination coating comprises a non-conductive alumina coating disposed over a protective layer to electrically isolate the sensor element. In a preferred embodiment, an alumina or alumina-based coating is disposed over a magnesium aluminate protective layer, which is in turn disposed over an electrode on an outer surface of the sensor element. In order to induce an optimum insulating effect, the combination coating extends from an end on which an active area of the sensor element is located to a point proximate, and preferably at, the opposing end of the sensor element. The active area of the sensor element is that portion thereof that is contactable by the flow of exhaust gas. The use of the alumina coating over the magnesium aluminate poison resistance layer on the sensor element yields higher quality, more durable, and more reliable isolative properties than does a configuration of a magnesium aluminate coating alone.

Figure 1:
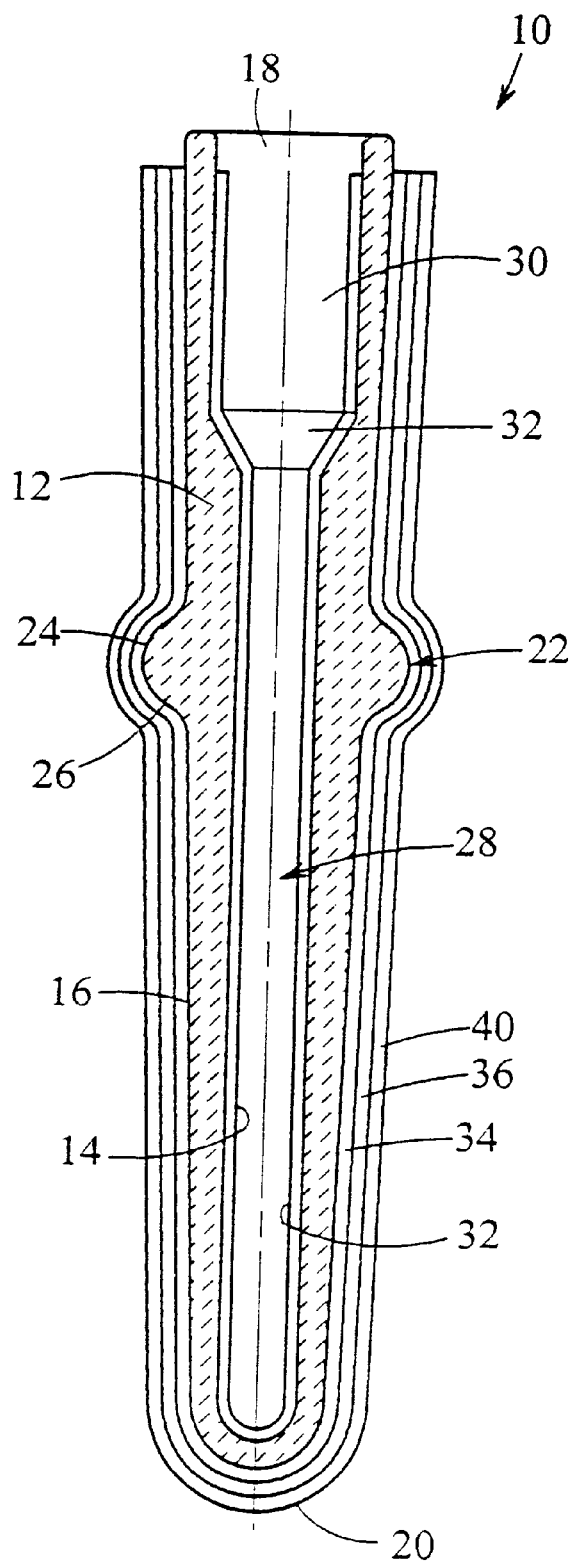
FIG. 1 is a side elevation sectional view of an embodiment of a gas sensor.

Referring now to FIG. 1, the sensor element is shown generally at 10. Sensor element 10 typically comprises an electrolyte body, shown generally at 12, having an inner surface 14, an outer surface 16, a cavity opening 18 located at one end of electrolyte body 12, and a cavity terminus 20 located at an opposing end of electrolyte body 12. An inner electrode 32 is disposed on inner surface 14, and an outer electrode 34 is disposed on outer surface 16. A protective layer 36 is disposed over outer electrode 34, and a combination poison resistant/ground isolating coating 40 is disposed over protective layer 36. In a preferred embodiment, protective layer 36 is deposited on and extends over the active area of sensor element 10, and more preferably, extends over substantially the entire outer surface of the sensor element 10.

Sensor element 10 can be formed in any generally cylindrical shape and is preferably tapered from cavity opening 18 to cavity terminus 20. A protrusion 22 is typically formed on sensor element 10 at a point intermediate cavity opening 18 and cavity terminus 20 to define an upper shoulder 24 and a lower shoulder 26 that preferably extends completely around the circumference of a cross section of electrolyte body 12. Protrusion 22 is generally configured and dimensioned to engage a surface within a shell portion (not shown) of the gas sensing apparatus into which sensor element 10 is received, thereby causing the inactive portion of the sensor, e.g., the portion above and including the lower shoulder 26, to extend out of the shell portion while the active portion extends into the shell portion to contact the exhaust gas.

Possible materials used for electrolyte body 12 include conventional materials well known in the art, e.g., metal oxides and the like, such as zirconia, and the like, which may optionally be stabilized with yttrium, aluminum, calcium, magnesium, lanthanum, cesium, gadolium, barium, among others, and combinations, alloys, and oxides comprising at least one of the foregoing electrolyte materials, with a zirconia/yttria/alumina mixture being preferred. Other additives that can be incorporated into the electrolyte body 12 include, but are not limited to, binders, waxes, and organic powders. The foregoing additives can also be added to improve the performance characteristics of sensor element 10.

A cavity, shown generally at 28, is defined by the contours of inner surface 14. Cavity 28 can be of any shape that enables electrical connection to sensor element 10, such as a generally cylindrical geometry. Preferably, cavity 28 has an upper portion 30 that can be generally cylindrical and is joined to the main body portion of cavity 28 with a tapered portion 32. Upper portion 30 allows an electrode clip (not shown) to be frictionally received in cavity 28, thereby allowing for the connection of a wiring harness (not shown) to sensor element 10. The main body portion of cavity 28 is configured to be narrower in cross-section than upper portion 30 in order to minimize the gap between a heating element (not shown) typically inserted into sensor element 10 and extending into cavity 28.

Figure 2:
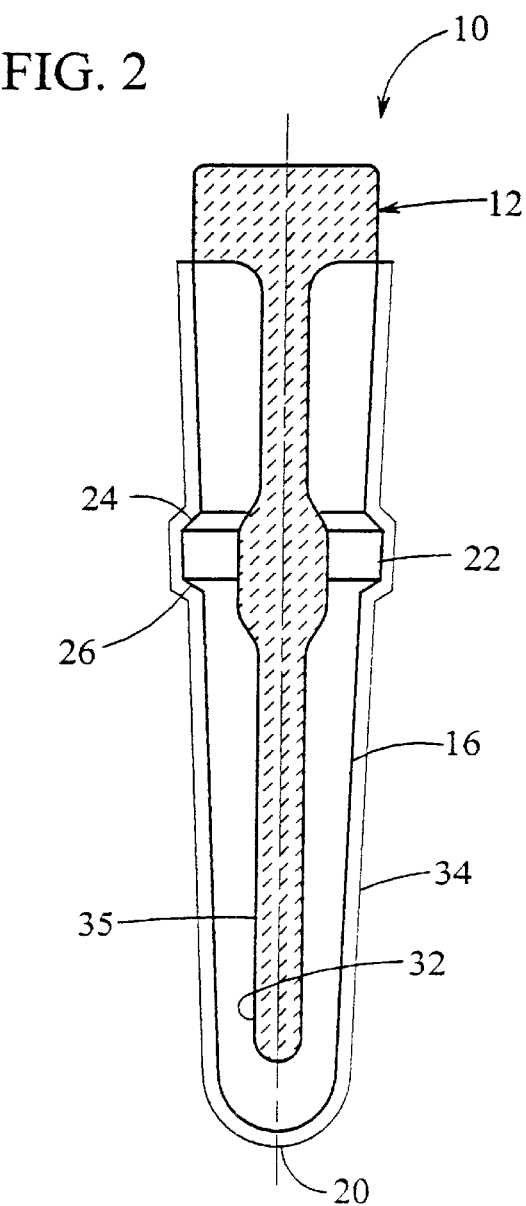
FIG. 2 is a side elevation sectional view of the formation of an inner electrode on an inner surface of an electrolyte body using an ink striping method.

Referring now to FIG. 2, inner electrode 32 is shown being disposed on inner surface 14 of electrode body 12. Electrodes 32, 34 can comprise any metallic catalyst capable of ionizing oxygen including, but not being limited to, materials such as platinum, palladium, iridium, rhodium, osmium, ruthenium, gold, osmium, zirconium, yttrium, cerium, calcium, aluminum, and the like, as well as oxides, mixtures, and alloys comprising at least one of the foregoing materials. Inner electrode 32 can be formed on electrolyte body 12 by any conventional technique, such as an ink striping process, which is well known in the art. Essentially, the metallic catalyst can be combined with a vehicle, which is usually an organic compound to form an electrode ink 35. As shown in FIG. 2, cavity 28 is filled with electrode ink 35, which adsorbs onto inner surface 14. The thickness of inner electrode 32 can be up to about 15 microns or so, with a thickness of about 8 to about 12 microns preferred to control the resistance and therefore reduce the heater wattage requirements.

As with inner electrode 32, outer electrode 34 can be formed with the same or a different ink. For example, outer electrode 34 can be formed on outer surface 16 by applying electrode ink 35 thereto using a conventional technique, such as spraying, painting, dipping, pad printing, or a similar method, and allowing electrode ink 35 to adsorb onto electrolyte body 12. In contrast to inner electrode 32, outer electrode 34 preferably has a thickness of about 10 microns or greater, with about 10 to about 30 microns more preferred, with a maximum resistance preferably of about 7.5 ohms or less. After vehicle adsorption, electrodes 32, 34 are not in electrical communication with one another, being present on inner surface 14 and outer surface 16, respectively, of electrolyte body 12.

Figure 3:
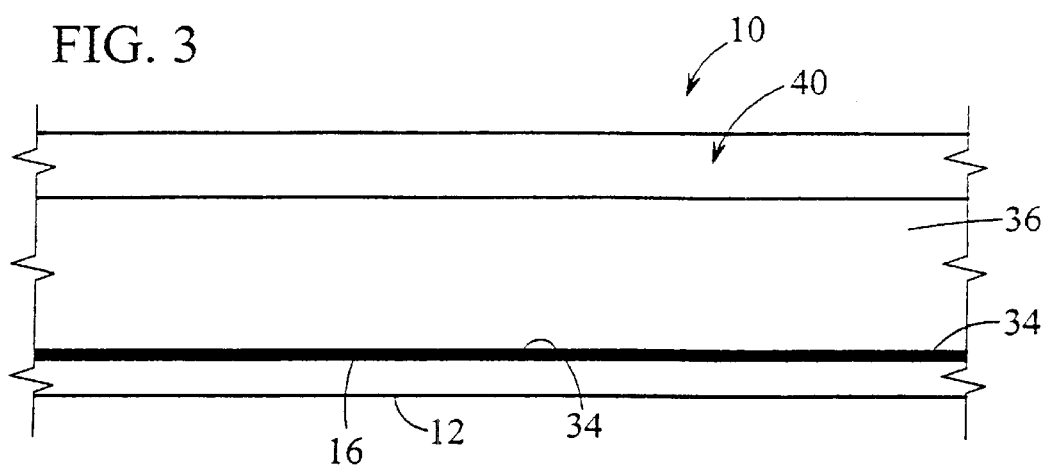
FIG. 3 is an enlarged view of the cross-section of the outer surface of the sensor element showing the ground isolating coating.

FIG. 3 is an enlarged sectional view of the outer surface of sensor element 10 at a point below protrusion 22. Electrode 34 is completely formed on outer surface 16. Protective layer 36 comprises a porous material and is typically applied to outer surface 16 of electrolyte body 12 over outer electrode 34. Any porous material that allows passage of exhaust gases while preventing the passage of unwanted contaminants can be used for protective layer 36.

Although this protective layer can be applied in any conventional manner, the preferred method of depositing protective layer 36 is plasma spraying. Typically, the protective layer is applied to a thickness of about 50 to about 200 microns, with a thickness of about 90 to about 140 microns being preferred. Possible materials for the protective coating 36 include magnesium aluminate, ceramic, glass, zirconia, and the like, as well as combinations comprising at least one of the foregoing materials.

Over protective layer 36 is a combination poison resistant/ground isolation coating shown generally at 40. This combination coating 40, which minimizes the effects of transient voltage spikes, thereby minimizing the chances that the sensor output voltage will be adversely affected by differences in sensor ground potential and exhaust system ground potential, can comprise a dielectric material. Possible materials for the combination coating 40, include alumina, (such as, delta alumina, gamma alumina, theta alumina, and the like, and combinations comprising at least one of the foregoing aluminas), as well as other dielectric materials.

Combination coating 40 can be deposited on the protective layer 36 through a variety of processes including, but which are not limited to, ceramic tape casting methods, colloidal dipping, painting, screen-printing, stenciling, plasma spray deposition, colloidal spray deposition, and the like, with colloidal dipping preferred. Preferably, the alumina has a density and thickness sufficient to provide poison resistance and render it substantially hydrophobic, with the overall combined thickness of the combination coating 40 and the protective layer 36 being ultimately dictated by the overall sensor design; namely the shell size. Typically the combined thickness is up to about 250 microns ($\mu$) or so, with up to about 150$\mu$ preferred. Preferably, the alumina has a thickness of up to about 120$\mu$, with about 10$\mu$ to about 50$\mu$ more preferred, and about 10$\mu$ to about 35$\mu$ especially preferred.

Once combination coating 40 is deposited onto sensor element 10, the manufacture of sensor element 10 is completed with a heat treatment in a an inert atmosphere, such as a pure nitrogen atmosphere, for a time sufficient to reduce the statistical variation associated with the performance of sensor element 10. The time required for such a reduction is typically about an hour or so, with about 0.5 hours to about 1.0 hours generally employed at a temperature of about 600° C. to about 1,000° C., with about 700° C. to about 900° C. being preferred.

The completed sensor element is then incorporated into the gas sensing apparatus through conventional means, which is typically the insertion of a heater into the sensor element adjacent the inner electrode, the insertion of the sensor element into a portion, the attachment of the wiring harness, and the attachment of an upper shield sealing the sensor element into the shell.

The results of breakdown tests of isolated ground parts are shown for a combination coating 40 comprising an alumina coating over a magnesium aluminate coating and for a ground isolating coating of the prior art consisting of magnesium aluminate, with reference to Tables 1 and 2, respectively. Voltage breakdown occurs when the resistance for a given applied voltage across the coating drops abruptly and dramatically, as can be seen when comparing Table 1 with Table 2. The prior art coating of Table 2, like combination coating 40 of Table 1, extends from the cavity terminus of the sensor element over the protrusion (e.g., hips) to substantially cover the sensor element. As can be seen in Table 1, the breakdown voltage (V) is greater than 600 volts for sensor element 10 incorporating the combination coating 40. As can be seen in Table 2, the breakdown voltage is between 200 and 300 volts for a sensor element of the prior art having only the standard magnesium aluminate coating.

TABLE 1

Breakdown test of isolated ground parts: alumina coating over magnesium aluminate poison resistance coating

| Breakdown voltage (V) | Time (min) | Current ($\mu$A)[1] | Resistance (M$\Omega$)[2] |
|---|---|---|---|
| 100 | 0 | 75.2 | 1.3 |
|  | 0.5 | 78.9 | 1.3 |
|  | 1 | 80.7 | 1.2 |
|  | 2 | 82 | 1.2 |
|  | 3 | 82.1 | 1.2 |
|  | 4 | 81.8 | 1.2 |
|  | 5 | 81.3 | 1.2 |
| 200 | 0 | 165.4 | 1.2 |
|  | 1 | 162.9 | 1.2 |
|  | 2 | 160 | 1.3 |
|  | 3 | 156 | 1.3 |
|  | 4 | 151.6 | 1.3 |
|  | 5 | 147.3 | 1.4 |
| 300 | 0 | 223.3 | 1.3 |
|  | 1 | 215.6 | 1.4 |
|  | 2 | 209.4 | 1.4 |
|  | 3 | 203.2 | 1.5 |
|  | 4 | 197.1 | 1.5 |
|  | 5 | 191.8 | 1.6 |
| 400 | 0 | 259.8 | 1.5 |
|  | 1 | 252.3 | 1.6 |
|  | 2 | 246.4 | 1.6 |
|  | 3 | 240.6 | 1.7 |
|  | 4 | 235.5 | 1.7 |
|  | 5 | 230.9 | 1.7 |
| 500 | 0 | 293.4 | 1.7 |
|  | 1 | 289.3 | 1.7 |
|  | 2 | 284.6 | 1.8 |
|  | 3 | 280 | 1.8 |
|  | 4 | 275.8 | 1.8 |
|  | 5 | 271.4 | 1.8 |
| 600 | 0 | 330.8 | 1.8 |
|  | 1 | 328.6 | 1.8 |
|  | 2 | 323.9 | 1.9 |
|  | 3 | 319.4 | 1.9 |
|  | 4 | 314.9 | 1.9 |
|  | 5 | 310.7 | 1.9 |

[1]$\mu$A - micro Amperes
[2]M$\Omega$ - mega ohms

TABLE 2

Breakdown test of isolated ground parts: standard magnesium aluminate coating

| Breakdown voltage (V) | Time (min) | Current ($\mu$A) | Resistance (M$\Omega$) |
|---|---|---|---|
| 100 | 0 | 205 | 0.5 |
|  | 1 | 53.5 | 1.9 |
|  | 2 | 39.1 | 2.6 |
|  | 3 | 32.2 | 3.1 |
|  | 4 | 27.8 | 3.6 |
|  | 5 | 24.7 | 4.0 |
| 200 | 0 | 68.2 | 2.9 |
|  | 1 | 65.3 | 3.1 |
|  | 2 | 54.9 | 3.6 |
|  | 3 | 48.4 | 4.1 |
|  | 4 | 44.1 | 4.5 |
|  | 5 | 41 | 4.9 |
| 300 | 0 |  | 0.0011 |

Comparing 1 and Table 2, the breakdown voltage for a sensor element having a combination coating of alumina 40 is greater than a sensor element having only a standard magnesium aluminate coating, as is evident from the lower breakdown voltage of the sensor element having the pure magnesium aluminate as the ground isolating coating.

Consequently, a sensor element incorporating the combination alumina coating 40 enables the sensor element to withstand increased voltages before breaking down (e.g., voltages of about 350 volts or greater, with about 450 volts or greater preferred, and about 600 volts or greater especially preferred).

The deposition of combination coating 40 over the protective layer 36 has advantages over the configurations of the prior art. In particular, if the combination coating 40 is an alumina layer, the deposition thereof over a magnesium aluminate poison resistance layer costs less than a additional ceramic spacer component. Furthermore, an alumina layer costs less and is easier to process than a glass ground-isolating layer. Essentially, the use of the ground isolating coating has enabled more than a 100% improvement over a conventional magnesium aluminate in breakdown voltage, namely from 200 to 300 volts (conventionally) to greater than about 600 volts (with the combination coating). This increased breakdown voltage has been correlated to increased durability and reliability in the specified application.

While preferred embodiments have been shown and described, various modifications and substitutions may be made thereto without departing from the spirit and scope of the invention, including the use of the geometries taught herein in other conventional sensors. Accordingly, it is to be understood that the apparatus and method have been described by way of illustration only, and such illustrations and embodiments as have been disclosed herein are not to be construed as limiting to the claims.

We claim:

1. An exhaust gas sensor element, comprising:

an electrolyte having a tip and a protrusion;

an inner electrode disposed on an inner surface of said electrolyte body;

an outer electrode disposed on an outer surface of said electrolyte body from said tip toward said protrusion;

a protective layer disposed over said outer electrode; and an alumina coating disposed directly over at least a portion of said protective layer and extending over said protrusion to electrically isolate the sensor element.

2. The gas sensor element of claim 1, wherein said alumina is selected from the group consisting of gamma alumina, theta alumina, and mixtures comprising at least one of the foregoing aluminas.

3. The gas sensor element of claim 2 wherein said alumina coating has a thickness of up to about 120 microns.

4. The gas sensor element of claim 3, wherein said thickness is about 5 microns to about 50 microns.

5. The gas sensor element of claim 4, wherein said thickness is about 10 microns to about 35 microns.

6. The gas sensor element of claim 1, wherein the sensor element has a breakdown voltage of about 350 volts or greater.

7. The gas sensor element of claim 6, wherein the breakdown voltage is about 450 volts or greater.

8. The gas sensor element of claim 7, wherein the breakdown voltage is about 600 volts or greater.

9. The gas sensor element of claim 1, wherein said protective layer has a thickness of about 50 microns to about 200 microns.

10. The gas sensor element of claim 9, wherein said protective layer has a thickness of about 90 microns to about 140 microns.

11. The gas sensor element of claim 1, wherein said protective layer is a material selected from the group consisting of magnesium aluminate, ceramic, glass, zirconia and combinations comprising at least one of the foregoing materials.

12. The gar sensor of claim 11, wherein the protective layer comprises magnesium aluminate.

13. The gas sensor element of claim 1, wherein said alumina coating is substantially hydrophobic.

14. The gas sensor element of claim 1, wherein said alumina coating covers said tip.

* * * * *